United States Patent [19]

McFarlane

[11] Patent Number: 5,181,909
[45] Date of Patent: Jan. 26, 1993

[54] AMPULE-CONTAINER MEDICAL SYRINGE AND METHODS

[76] Inventor: Richard H. McFarlane, 2571 Kaneville Rd., Geneva, Ill. 60134

[21] Appl. No.: 699,622

[22] Filed: May 15, 1991

[51] Int. Cl.⁵ .......................................... A61M 31/00
[52] U.S. Cl. ..................................... 604/52; 604/200;
  604/191; 604/226; 604/220; 604/87
[58] Field of Search ............ 604/83, 87, 110, 183–185,
  604/187, 191, 193, 194, 199, 200, 213, 220, 226,
  231, 232, 236, 237, 52

[56] References Cited

U.S. PATENT DOCUMENTS

| | | | |
|---|---|---|---|
| 1,563,627 | 12/1925 | Hein | 604/226 |
| 1,744,893 | 1/1930 | Hein | 604/200 X |
| 2,764,979 | 10/1956 | Henderson | 604/200 X |
| 2,907,328 | 10/1959 | Cohen | 604/226 X |
| 3,040,743 | 6/1962 | Naess | 604/200 X |
| 3,506,006 | 4/1970 | Lange, Jr. | 604/200 X |
| 3,659,749 | 5/1972 | Schwartz | 604/87 X |
| 3,835,835 | 9/1974 | Thompson et al. | 604/191 X |
| 4,271,835 | 6/1981 | Conn et al. | 604/226 X |
| 4,412,836 | 11/1983 | Brignola | 604/87 |
| 4,693,706 | 9/1987 | Ennis, III | 604/87 |
| 4,861,335 | 8/1989 | Reynolds | 604/88 |
| 5,032,117 | 7/1991 | Motta | 604/88 |

Primary Examiner—John D. Yasko
Assistant Examiner—Adam J. Cermak
Attorney, Agent, or Firm—Malloy, Downey & Malloy

[57] ABSTRACT

A medical syringe has a plunger bore (1 and 2) that is flexible. A hermetically-sealed glass ampule (3) containing a drug in the form of a liquid referred to generally as a sterile preparation (4) is placed in the plunger bore (1 and 2). When the plunger (1) is pulled outwardly a select distance to expose the flexible plunger bore (2), the glass ampule (3) is broken by hand-squeezing the plunger bore (2) against it. Liquid preparation (4) from the glass ampule (3) is directed through a check-valved orifice (16) at a tip of a resilient piston section (21) of the plunger (1). At the check-valved orifice (16), the preparation (4) enters into a syringe bore (6). There the preparation (4) can be injected through a conventional luer (38–40) and hypodermic needle (37) by the standard practice of depressing the plunger (1) into the syringe (7). Variations are provided for storing ampules of preparation either in or separately from the syringe. Embodiments are described for various adaptations. Use methods are described.

31 Claims, 4 Drawing Sheets

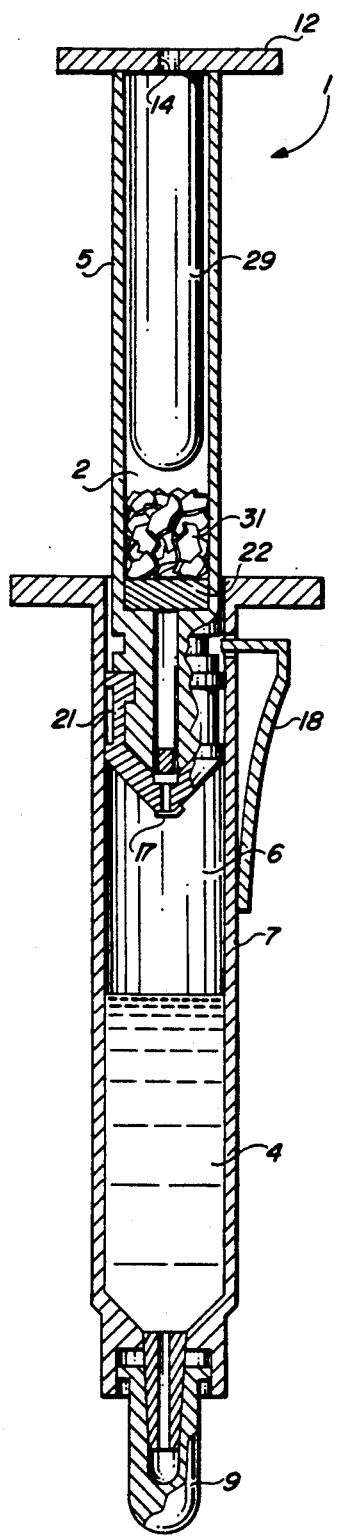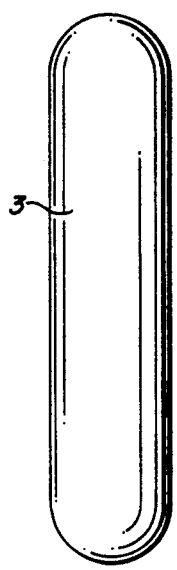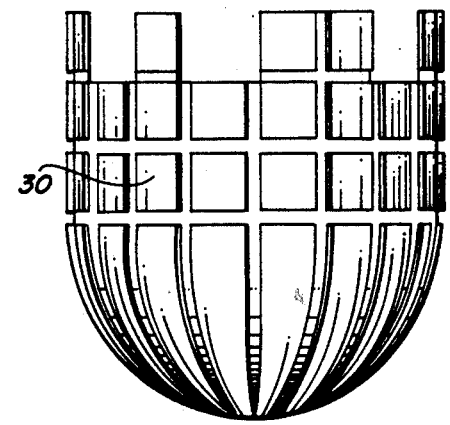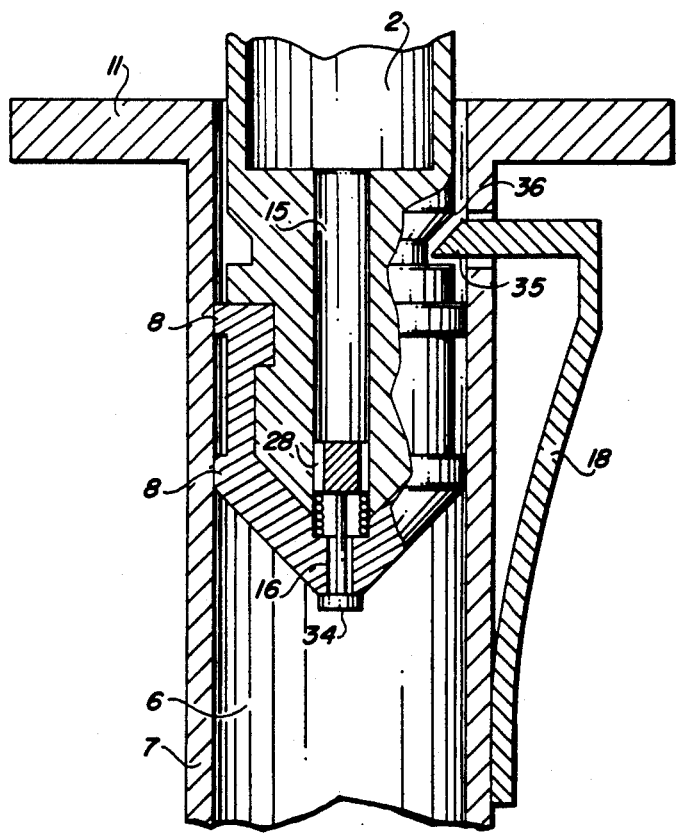
FIG-7
FIG-8
FIG-9
FIG-10

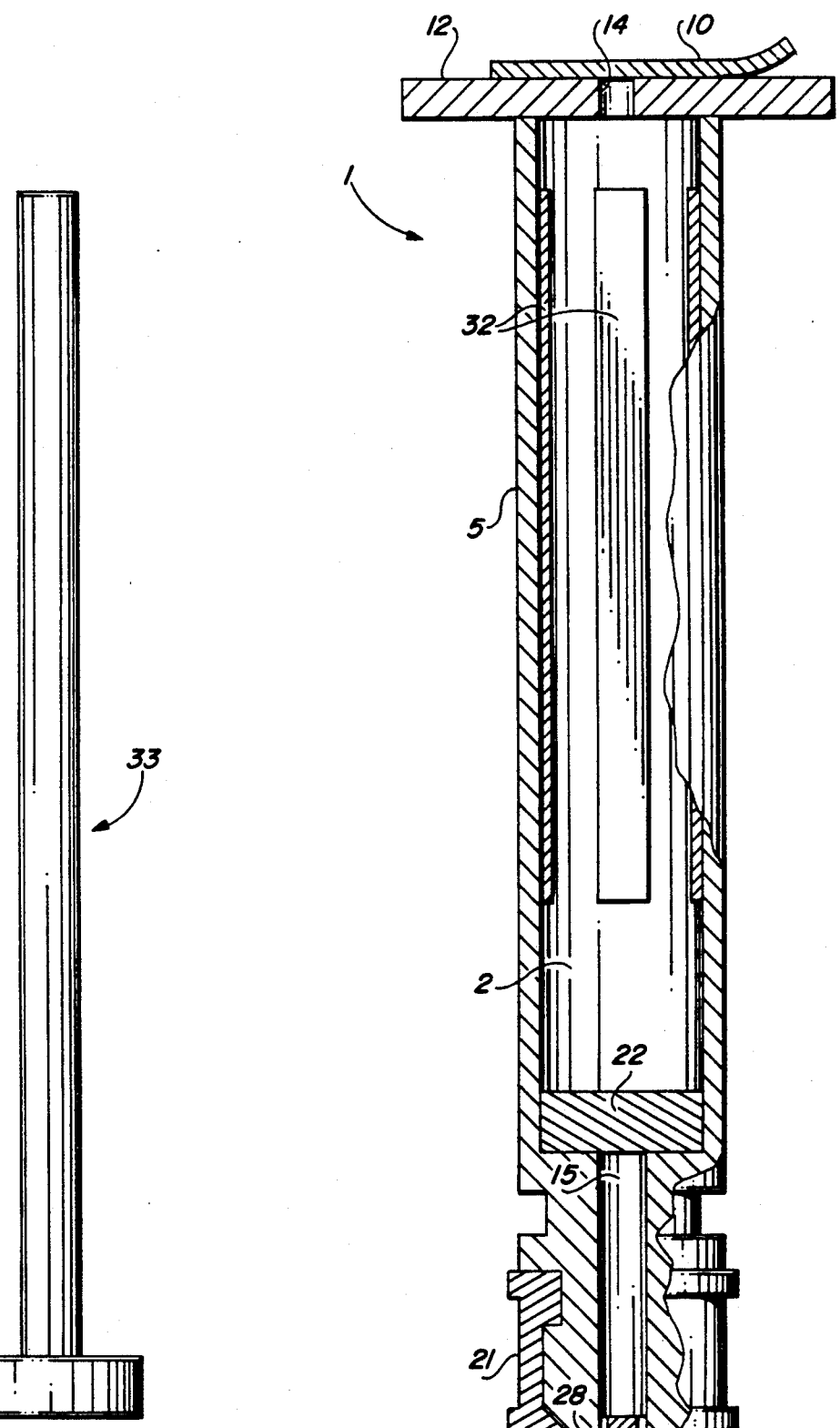

AMPULE-CONTAINER MEDICAL SYRINGE AND METHODS

BACKGROUND OF THE INVENTION

1. Field of the Invention

This invention relates to medical syringes. More particularly, it relates to a syringe having a plunger bore that is flexible against an internal glass ampule containing a drug to break the ampule and direct the drug into a syringe bore.

2. Description of Related Art

A wide variety of medical syringes have been devised to optimize time and convenience in relation to storage, use and prevention of contamination dangers. But none are known or believed to exist with a means for containing a glass ampule inside the syringe where it is fractured to allow a sterile preparation to be directed from the ampule into the syringe for injection.

Shelf-life of preparations in hermetically-sealed ampules is many times longer than for those stored in plastic or other types of containers. However, a hermetically-sealed glass container is difficult to use. There has been no convenient and sanitary method for transferring its contents into a syringe. Consequently, glass ampules often have sections which are openable by various means. But any non-glass section decreases contaminating or porous surface area of the ampule, rather than eliminating it totally. This invention solves the problem of injecting sterile preparations contained in hermetically-sealed glass ampules.

SUMMARY OF THE INVENTION

A medical syringe has a hollow plunger shaft that is flexible. A hermetically-sealed glass ampule containing a drug in the form of a liquid referred to generally as a sterile preparation is placed in the hollow plunger shaft. When the plunger is pulled outwardly a select distance to expose the flexible hollow plunger shaft, the glass ampule is broken by hand-squeezing the plunger shaft against it. Liquid preparation from the glass ampule is directed through a check-valved orifice at a tip of a resilient piston section of the plunger. At the check-valved orifice, the preparation enters into a syringe bore. There the preparation can be injected through a conventional luer and hypodermic needle by the standard practice of depressing the plunger into the syringe. Variations are provided for storing ampules of preparation either in or separately from the syringe. Embodiments are described for various adaptations. Use methods are described.

BRIEF DESCRIPTION OF THE DRAWINGS

This invention is described by appended claims in relation to description of a preferred embodiment with reference to the following drawings wherein:

FIG. 7 is a cutaway elevation view of a disposable-syringe embodiment having a different means for isolating sterile preparation from ambient air.

FIG. 8 is a side elevation view of a conventional ampule of the type used in this invention.

FIG. 9 is a sectional cutaway side view of a fragmentation ampule for breaking into shaped fragments without sharp edges or minute particles.

FIG. 10 is an exploded sectional cutaway side view of a plunger piston with an embodiment of a locking means and value means.

FIG. 11 is an elevation view of a mallet constructed as an aid in breaking glass ampules.

FIG. 12 is a cutaway elevation view of a plunger having metallic or other hard internal ridges for breaking glass ampules.

DESCRIPTION OF PREFERRED EMBODIMENT

Figure 1:
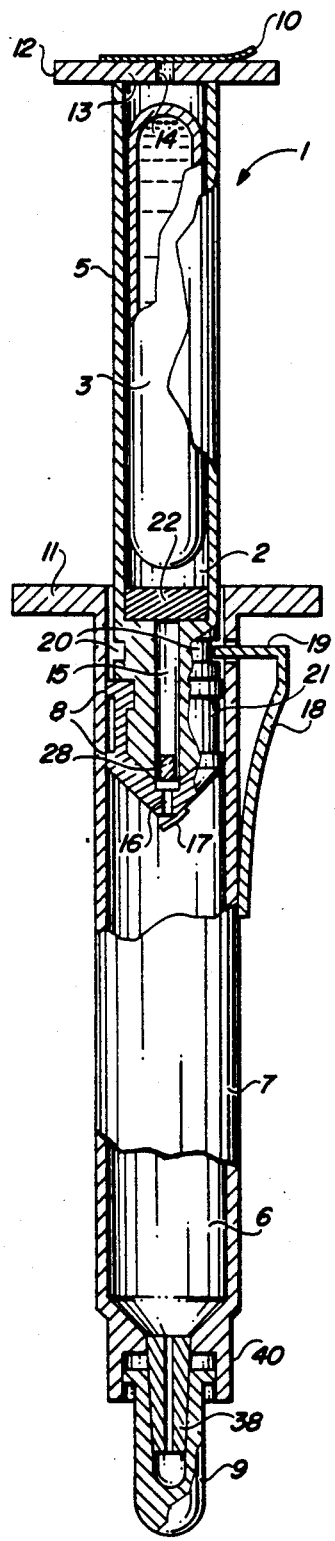
FIG. 1 is a cutaway elevation view of a disposable-syringe embodiment of the invention containing an ampule of sterile preparation in a plunger bore.

Reference is made to FIG. 1. A syringe plunger 1 has a plunger bore 2 into which is insertable a glass ampule 3 containing a drug in the form of a liquid referred to as a sterile preparation 4.

Plunger walls 5 of the plunger bore 2 are flexible inwardly by hand-squeezing or other method to break the ampule 3 when the plunger bore 2 is pulled outwardly from syringe bore 6 of syringe barrel 7.

As the syringe plunger 1 is pulled outwardly from the syringe barrel 7, negative pressure is caused in the syringe bore 6 as a result of changing volume sealed by a combination of plunger piston rings 8, luer shank seal 9 and plunger grip seal 10. The syringe plunger is pulled outwardly by gripping syringe handle 11 and plunger handle 12. The luer shank seal 9 can be in the form of a blind hypodermic needle holder as illustrated.

At the plunger handle 12 there is a plunger-bore plate 13 with a pressure-equalizer orifice 14 that is sealable by plunger grip seal 10 which can be in the form of an adhesive peal-away sheet or other convenient covering means. Negative pressure in the plunger bore 2 and in the syringe bore 6 is equalized by fluid communication through piston bore 15 and tip port 16 having one-way valve 17 in check-valve relationship to fluid flow from the plunger bore 2 into the syringe bore 6. The syringe plunger 1 can be held conveniently in this negative bore-pressure condition by depressing lever 18 to insert latch 19 into latch notch 20.

The ampule 3 is broken by squeezing plunger walls 5 while the syringe barrel 7 is held at an attitude that positions the ampule 3 above the syringe barrel 7 and while the negative bore-pressure is maintained with the latch 19 in the latch notch 20. A vertical or near vertical attitude is preferable.

These conditions cause a head of preparation 4 fluid to flow in the direction of plunger piston 21 and piston bore 15. Then when plunger grip seal 10 is removed or otherwise dislodged to uncover pressure-equalizer orifice 14, the sterile preparation flows past one-way valve 17 in syringe bore 6.

Figure 2:
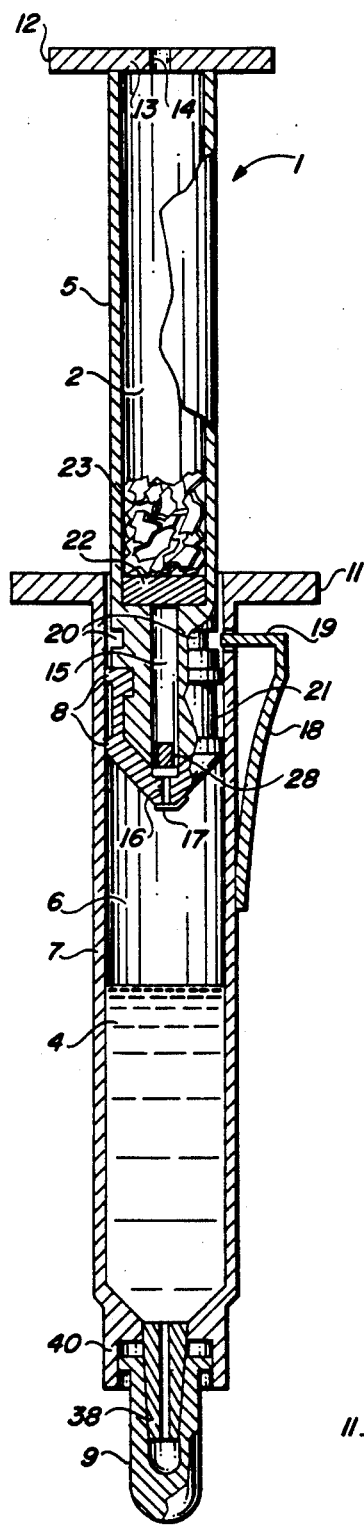
FIG. 2 is a cutaway elevation view of the FIG. 1 illustration after the ampule is broken and the sterile preparation is in the syringe bore.

Referring to FIGS. 1 and 2, fluid preparation 4 is filtered through filter 22 to prevent glass particles 23 from entering the syringe bore 6 where they could be injected with the preparation 4.

Figure 3:
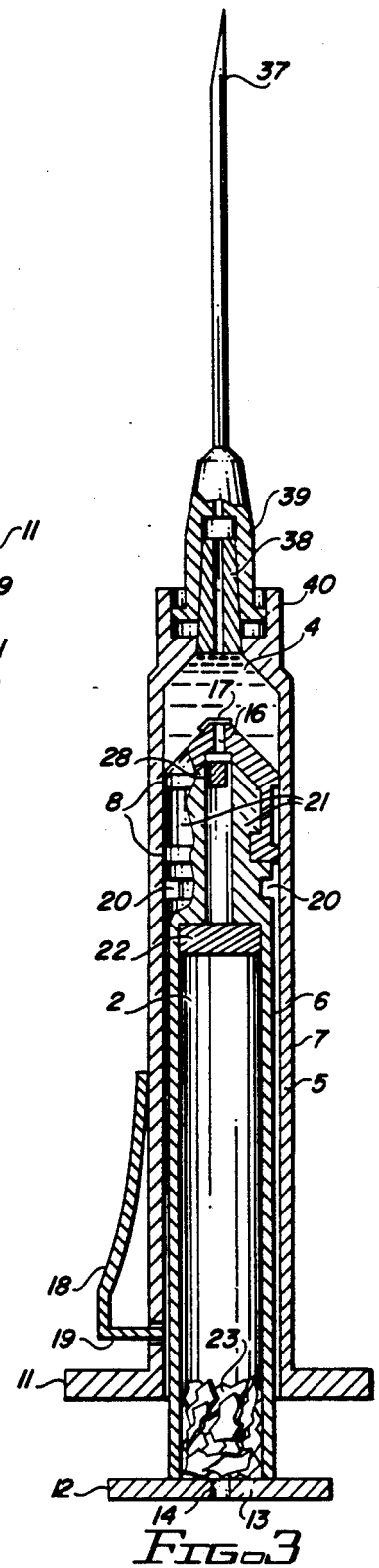
FIG. 3 is an inverted cutaway elevation view of an assembled FIG. 1 embodiment of the syringe in aspiration attitude.

Referring to FIG. 3, the sterile preparation 4 is prevented by one-way valve 17 from returning into syringe bore 6 when the syringe barrel 7 is aspirated in inverted attitude the same as for conventional syringes. Tightness of seal increases with injection pressure. The latch 19 is removed from latch notch 20 and glass particles 23 fall to the vicinity of plunger-bore plate 13 where they can be contained securely if desired by replacing a peal-away plunger-grip seal 10.

The embodiment of the invention shown in FIGS. 1-3 is intended to be a disposable syringe. For this purpose, it is preferable that the plunger-bore plate 13 be made of glass or other material which is breakable into fragments which cannot be reassembled if broken to be reused with another ampule of preparation 4. The ampule 3 can be stored in the plunger bore 2 with the syringe plunger 1 and syringe barrel 7 assembled. The ampule 3 of preparation 4 is stored in a form that it can be injected with a disposable means using this embodiment of the invention.

Figure 4:
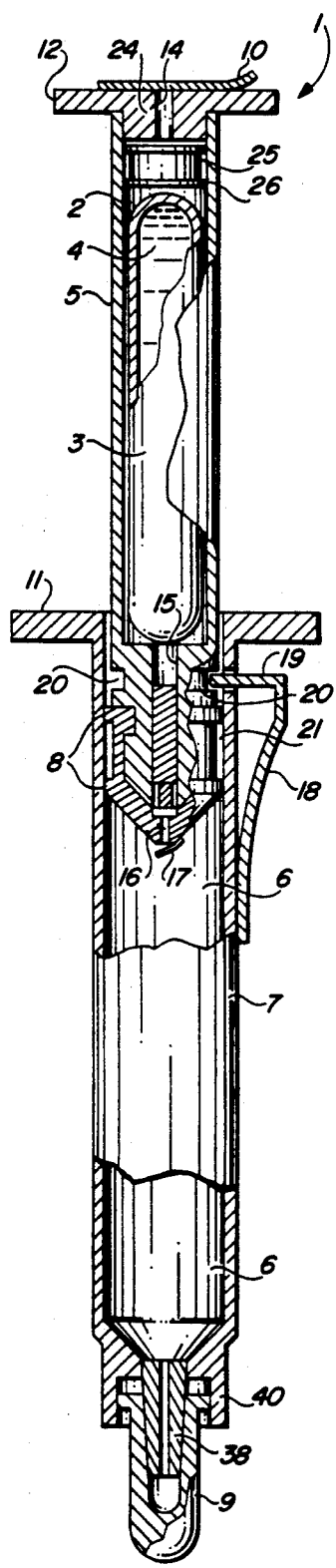
FIG. 4 is a cutaway elevation view of an embodiment of the invention having a means for isolating the sterile solution from ambient air in the syringe, that is storable separately from ampules and is optionally reusable.
Figure 5:
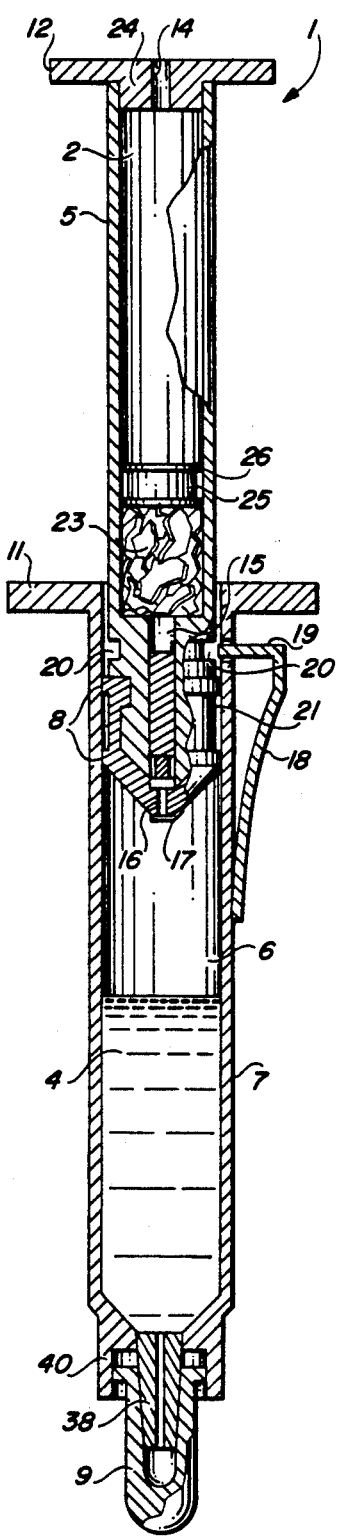
FIG. 5 is a cutaway elevation view of the FIG. 4 embodiment after sterile preparation has been transferred to the bore of the syringe.
Figure 6:
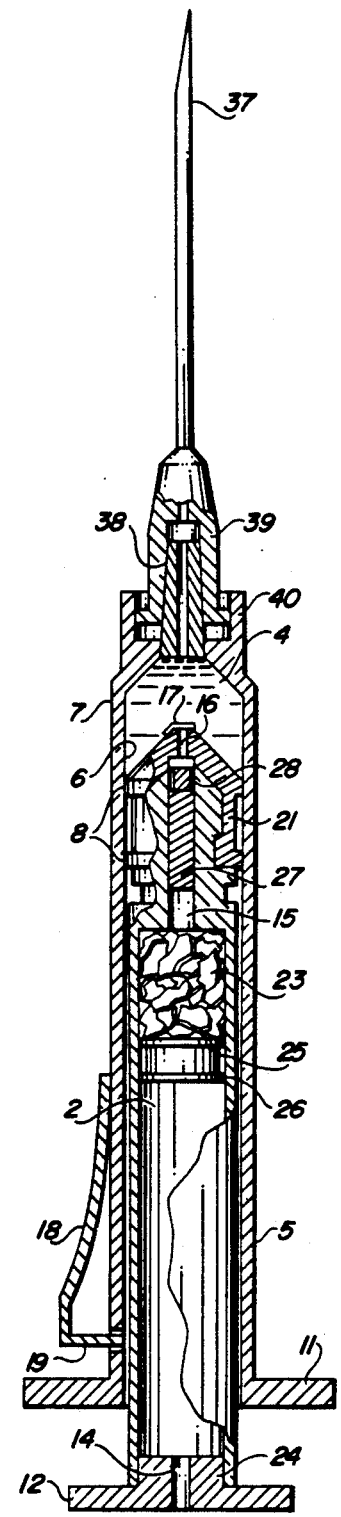
FIG. 6 is an inverted cutaway elevation view of an assembled FIG. 4 embodiment in aspiration attitude.

Referring to FIGS. 4-6, the ampule 3 of preparation 4 can be stored separately and inserted into plunger bore 2 when desired by removing an attachable plunger lid 24 and replacing it after the ampule 3 has been placed in the plunger bore 2. All other features, components and adaptations can be the same for the different embodiments. Appropriate sanitation is assumed for both syringe storage or separate storage and injection of preparation 4 in ampule 3.

Preparation 4 can be isolated from ambient air by a free piston 25 having free-piston rings 26. The free piston 25 is inserted in the plunger bore 2 after insertion of the ampule 3. The free piston 25 is actuated by negative pressure to travel towards the plunger piston 21 after the plunger grip seal 10 has been opened. As it travels in that direction, the free piston 25 wipes preparation 4 from inside surfaces of plunger walls 5 and carries it in the direction of the syringe bore 6 for a more complete use of the preparation. Free piston 25 also prevents glass fragments from falling out through pressure-equalizer orifice 14 during aspiration and use.

Referring further to FIGS. 4-6, a piston-bore filter 27 can be a cylindrical member insertable in piston bore 15. In addition to filter 27 or filter 22, there can be small tubular conveyances 28 positioned between plunger bore 2 and tip port 16 as illustrated in FIGS. 1-7. This further prevents particles of glass 23 from entering the syringe bore 6. Optionally also, a filter 22 can be relatively porous and used in conjunction with filter 27 that can be finer and longer for filtering finer particles. Any appropriate form and combination of filters can be used with or without the small tubular conveyances 28.

Referring to FIG. 7, a balloon 29 can be attached to the plunger-bore plate 13 to contain ambient air entering through pressure-equalizer orifice 14 and prevent it from contaminating the preparation 4. However, it may be fractured by glass fragments 23 unless relatively tough material is used for its construction.

Referring to FIGS. 7-9, a conventional ampule 3 intended for use with this invention has smooth walls. Optionally, however, fragmentation walls 30 with thin-walled break channels therebetween may be employed to cause smooth-edged glass particles 31 as illustrated in FIG. 7. Smooth-edged glass 31 is an optional advantage for all embodiments of this invention but is not necessary with adequate filters 22 and 27 and with adequate breakage of the ampule 3 by squeezing plunger walls 5.

Metallic strips 32, shown in FIG. 12, can be provided on the inside of plunger walls 5 to aid in breaking the glass ampule 3 whether having conventional smooth walls or fragmented walls 30. However, metallic strips 32 are a tradeoff option to a free piston because they would tend to prevent sealing of free-piston rings 26.

Referring to FIG. 11, optionally also for use particularly with the attachable plunger lid 24 is a mallet 33 which can be variously shaped. It can be employed directly against glass of the ampule 3 or against the free piston 25.

Referring to FIG. 10, a spring-actuated poppet valve 34 is optional to a conventional flapper valve, also known as a reed valve, illustrated in FIGS. 1-7 at the tip port 16 as the one-way valve 17.

The lever 18 to which the latch 19 is attached in FIGS. 1-7 can be biased outwardly such that it must be depressed and held to keep the plunger 1 in place in a drawn condition while breaking the ampule 3 and causing the mixture 4 to flow into the syringe bore 7. Optionally, the lever 18 can be biased inwardly such that it automatically prevents the plunger 1 from being withdrawn from the syringe bore 7. As an additional convenience, a beveled latch 35 on an inwardly-biased lever 18 can automatically prevent inward travel of the plunger 1 also unless a designed amount of pressure is applied on the plunger 1 to push it into the syringe bore 6. A beveled notch 36 can be employed in combination with or in lieu of beveled latch 35.

This invention employs accepted professional use of a conventional hypodermic needle 37 and the highly-reliable tapered luer shank 38 on which a hypodermic needle sheath 39 is retained by inside-diameter threads in a luer sleeve 40.

A new and useful ampule-container medical syringe and use methods having been described, all such modification, adaptations, applications and forms thereof described by the following claims are included in this invention.

What is claimed is:

1. An ampule-container syringe having:
    a syringe barrel with a syringe bore and a sealable luer, said bor having an injection conveyance in fluid communication with said sealable luer for attaching hypodermic needles at an injection end and suitable gripping means at a plunger-receiving end with a plunger-receiving orifice;
    a syringe plunger defining an axis and insertable into the syringe bore through the plunger receiving orifice;
    said plunger including a hollow plunger shaft having flexible walls defining a plunger bore sized and shaped to receive desired sizes and shapes of ampules in desired size relationships between the plunger bore and the ampules;
    a plunger tip in sliding-seal relationship to inside peripheral walls of the syringe bore;
    a plunger tip port having a one-way valve in one-way-valved relationship to flow of fluid from inside of the hollow plunger into the syringe bore;
    suitable plunger gripping means and an ampule-insertion orifice at a handle end of the syringe plunger; and
    a restraining means associated with said plunger for preventing escape of an ampule positioned in the hollow plunger shaft.

2. An ampule-container syringe according to claim 1 and further comprising:
 a plunger piston section constructed of appropriately resilient material at the tip end of the syringe plunger;
 a sliding-seal ring on the plunger piston section; and
 a piston fluid conveyance in communication between the plunger bore and the tip port.

3. An ampule-container syringe according to claim 1 and further comprising:
 a filter positionable between the plunger bore and the tip port.

4. An ampule-container syringe according to claim 3 and further comprising:
 a plunger piston section constructed of appropriately resilient material at the tip end of the syringe plunger;
 a sliding-seal ring on the plunger piston section; and
 a piston fluid conveyance in communication between the plunger bore and the tip port.

5. An ampule-container syringe according to claim 4 wherein the filter is in the form of a cylindrical wafer positioned proximate an entrance to the piston fluid conveyance.

6. An ampule-container syringe according to claim 4 wherein the filter is in the form of a cylinder positioned snugly inside of the piston fluid conveyance.

7. An ampule-container syringe according to claim 4 wherein a select portion of the piston fluid conveyance is comprised of a plurality of suitably small-diameter conveyance passages.

8. An ampule-container syringe according to claim 4 and further comprising:
 a plunger-latch notch positioned circumferentially proximate the plunger tip section on the syringe plunger; and
 a plunger latch positioned proximate the plunger-receiving end of the syringe engageable with the plunger-latch notch.

9. An ampule-container syringe according to claim 8 wherein the plunger latch is a lever arm constructed of resilient material with one end anchored to an outside peripheral portion on the syringe barrel and the opposite end having a lever angular member, said syringe barrel having an orifice therein, said lever angular member insertable through said orifice and into the latch notch when the syringe plunger is in a desired position in relationship to the plunger-receiving orifice in the plunger receiving end of the syringe.

10. An ampule-container syringe according to claim 9 wherein the plunger latch is biased outwardly from the syringe barrel.

11. An ampule-container syringe according to claim 9 wherein the plunger latch is biased inwardly towards the syringe barrel and further comprising:
 a proximal edge of the latch notch that is perpendicular to the axis of the plunger; and
 a distal edge of the latch notch which in combination with a proximal edge of the latch notch forms a suitably latch-raising angle of approximately 45 degrees from perpendicularity to the axis of the plunger.

12. An ampule-container syringe according to claim 1 wherein the restraining means for preventing escape of an ampule positioned in the hollow plunger shaft is a plunger-bore plate positionable in covering relationship to the plunger bore at the opposite end of the plunger shaft from the plunger tip.

13. An ampule-container syringe according to claim 12 and further comprising:
 a pressure-equalizer orifice in the plunger-bore plate.

14. An ampule-container syringe according to claim 13 and further comprising:
 a pressure-equalizer-orifice cover positionable on the plunger-bore plate in sealing relationship to the pressure-equalizer orifice.

15. An ampule-container syringe according to claim 14 and further comprising:
 a free-piston seal in sliding-seal relationship to inside linear walls of the plunger bore and positionable between the plunger-bore plate and an ampule placed in the plunger bore to provide a sanitary seal against contamination by airborne contaminants in air entering the plunger bore through the pressure-equalizer orifice.

16. An ampule-container syringe according to claim 15 wherein the restraining means for preventing escape of an ampule positioned in the hollow plunger shaft is a breakable plate constructed of material such as glass which breaks with dislodgement attempts in order to prevent subsequent use of the ampule-container syringe.

17. An ampule-container syringe according to claim 15 wherein the restraining means for preventing escape of an ampule positioned in the hollow plunger shaft is an attachable plunger lid such that ampules of sterile preparations can be stored separately from ampule-container syringes and then placed in plunger bores of the plunger shafts and the plunger lids are attached when the ampule-container syringe is used.

18. An ampule-container syringe according to claim 14 and further comprising:
 a balloon seal with entrance orifice surrounding the pressure-equalizer orifice and attached to an inside wall of the plunger-bore plate.

19. An ampule-container syringe according to claim 14 wherein the restraining means for preventing escape of an ampule positioned in the hollow plunger shaft is a breakable plate constructed of material such as glass which breaks with dislodgement attempts in order to prevent subsequent use of the ampule-container syringe.

20. An ampule-container syringe according to claim 14 wherein the restraining means for preventing escape of an ampule positioned in the hollow plunger shaft is an attachable plunger lid such that ampules of sterile preparations can be stored separately from ampule-container syringes and then placed in plunger bores of the plunger shafts and the plunger lids attached when the ampule-container syringe is used.

21. An ampule-container syringe according to claim 1 wherein the restraining means for preventing escape of an ampule positioned in the hollow plunger shaft is a breakable plate constructed of material such as glass which breaks with dislodgement attempts in order to prevent subsequent use of the ampule-container syringe.

22. An ampule-container syringe according to claim 1 wherein the restraining means for preventing escape of an ampule positioned in the hollow plunger shaft is an attachable plunger lid such that ampules of sterile preparations can be stored separately from ampule-container syringes and then placed in plunger bores of the plunger shafts and the plunger lids are attached when the ampule-container syringe is used.

23. An ampule-container syringe according to claim 1 and further comprising:
 a preparation-containing ampule sized and shaped to fit in desired relationship to inside dimensions of the bore of the syringe plunger and having an outside wall comprised of segmented components of a desired shape with thin-walled break channels between the segmented components.

24. An ampule-container syringe according to claim 23 wherein the segmented components are rectangular-shaped and have curved and smooth edges.

25. An ampule-container syringe according to claim 1 and further comprising:
   a plunger piston section constructed of appropriately resilient material at the tip end of the syringe plunger;
   a sliding-seal ring on the plunger piston section;
   a piston fluid conveyance in communication between the plunger bore and the tip port;
   a filter positionable between the plunger bore and the tip port;
   a portion of the piston fluid conveyance being comprised of a plurality of suitably small-diameter conveyances;
   a plunger-latch notch positioned circumferentially proximate the plunger tip section on the syringe plunger;
   a plunger latch positioned proximate the plunger-receiving end of the syringe engageable with the plunger-latch notch;
   the plunger latch being a lever arm constructed of resilient material with one end anchored to an outside peripheral portion on the syringe barrel and the opposite end having a lever angular member, said syringe barrel having an orifice therein, said lever angular member insertable through said orifice and into the latch notch when the syringe plunger is in a desired position in relationship to the plunger-receiving orifice in the plunger receiving end of the syringe;
   the plunger latch being biased outwardly from the syringe barrel;
   the restraining means for preventing escape of an ampule positioned in the hollow plunger shaft being a plunger-bore plate positionable in covering relationship to the plunger bore at the opposite end of the plunger shaft from the plunger tip;
   a pressure-equalizer orifice in the plunger-bore plate; and
   a pressure-equalizer-orifice cover positionable on the plunger-bore plate in sealing relationship to the pressure-equalizer orifice.

26. An ampule-container syringe according to claim 25 and further comprising:
   a free-piston seal in sliding-seal relationship to inside linear walls of the plunger bore and positionable between the plunger-bore plate and an ampule placed in the plunger bore to provide a sanitary seal against contamination by airborne contaminants in air entering the plunger bore through the pressure-equalizer orifice.

27. An ampule-container syringe according to claim 1 and further comprising:
   a plunger piston section constructed of appropriately resilient material at the tip end of the syringe plunger;
   a sliding-seal ring on the plunger piston section;
   a piston fluid conveyance in communication between the plunger bore and the tip port;
   a filter positionable between the plunger bore and the tip port;
   a portion of the piston fluid conveyance being comprised of a plurality of suitably small-diameter passageway conveyances;
   a plunger-latch notch positioned circumferentially proximate the plunger tip section on the syringe plunger;
   a plunger latch positioned proximate the plunger-receiving end of the syringe engageable with the plunger-latch notch;
   the plunger latch being a lever arm constructed of resilient material with one end anchored to an outside peripheral portion on the syringe barrel and the opposite end having a lever angular member, said syringe barrel having an orifice therein, said lever angular member insertable through said orifice and into the latch notch when the syringe plunger is in a desired position in relationship to the plunger-receiving orifice in the plunger receiving end of the syringe;
   the restraining means for preventing escape of an ampule positioned in the hollow plunger shaft being an attachable plunger lid such that ampules of sterile preparations can be stored separately from ampule-container syringes and then placed in plunger bores of the plunger shafts and the plunger lids are attached when the ampule-container syringe is used;
   a pressure-equalizer orifice in the plunger-bore plate; and
   a pressure-equalizer-orifice cover positionable on the plunger-bore plate in sealing relationship to the pressure-equalizer orifice.

28. An ampule-container syringe according to claim 1 and further comprising:
   metallic plates on the inside periphery of and linear to the axis of the syringe plunger.

29. An ampule-container syringe according to claim 1 and further comprising:
   a mallet sized and shaped for inserting into the plunger for selectively breaking the ampule.

30. A method for using an ampule-container syringe consisting of:
   a syringe barrel with a syringe bore having an injection conveyance in fluid communication with a sealable luer for attaching hypodermic needles at an injection end and suitable gripping means at a plunger-receiving end with a plunger-receiving orifice;
   a syringe plunger insertable into the syringe bore through the plunger receiving orifice;
   a hollow plunger shaft having flexible walls defining a plunger bore sized and shaped to receive desired sizes and shapes of ampules in desired size relationships between the plunger bore and the ampules;
   a plunger tip in sliding-seal relationship to inside peripheral walls of the syringe bore;
   a tip port having a one-way valve in one-way valved relationship to flow of fluid from inside of the hollow plunger into the syringe bore;
   suitable plunger gripping means and an ampule-insertion orifice at a handle end of the syringe plunger; and
   a restraining means for preventing escape of an ampule positioned in the hollow plunger shaft;
   comprising the following steps:
   positioning an ampule containing sterile preparation in a plunger-shaft bore of the syringe;

sealing the plunger-shaft bore with a breakable retaining cover;

storing the sterile preparation in the syringe bore of the syringe plunger of the syringe until a desired time before use;

positioning the syringe plunger in relationship to the syringe barrel such that a desired portion of flexible walls of the plunger shaft are exposed outside of the syringe bore;

positioning the syringe with the sealable luer in sealed condition lower than the plunger-bore plate;

hand-squeezing the flexible walls of the plunger shaft sufficiently to break the ampule within the plunger-shaft bore;

removing a pressure-equalizer cover from the plunger-bore plate;

allowing the sterile preparation to flow from the broken ampule into the syringe bore by means of a vacuum in the syringe bore and in the plunger bore in negative-pressure relationship to a fluid head of the sterile preparation;

reversing position of the syringe to where the sealable luer is above the plunger-bore plate;

unsealing the sealable luer, attaching a hypodermic needle to the sealable luer;

aspirating the syringe;

injecting the sterile preparation from the syringe as desired; and discarding the syringe appropriately.

31. A method for using an ampule-container syringe consisting of:

a syringe barrel with a syringe bore having an injection conveyance in fluid communication with a sealable luer for attaching hypodermic needles at an injection end and suitable gripping means at a plunger-receiving end with a plunger-receiving orifice;

a syringe plunger insertable into the syringe bore through the plunger receiving orifice;

a hollow plunger shaft having flexible walls defining a plunger bore sized and shaped to receive desired sizes and shapes of ampules in desired size relationships between the plunger bore and the ampules;

a plunger tip in sliding-seal relationship to inside peripheral walls of the syringe bore;

a tip port having a one-way valve in one-way valved relationship to flow of fluid from inside of the hollow plunger into the syringe bore;

suitable plunger gripping means and an ampule-insertion orifice at a handle end of the syringe plunger;

a restraining means for preventing escape of an ampule positioned in the hollow plunger shaft;

the restraining means for preventing escape of an ampule positioned in the hollow plunger shaft being an attachable plunger lid such that ampules of sterile preparations can be stored separately from ampule-container syringes and then placed in plunger bores of the plunger shafts and the plunger lids are attached when the ampule-container syringe is used;

comprising the following steps:

storing sterile preparation in an ampule separately from the ampule-container syringe;

positioning an ampule containing sterile preparation in a plunger bore at a desired time before use of the sterile preparation;

sealing the plunger-shaft bore with the attachable plunger lid;

positioning the syringe plunger in relationship to the syringe barrel such that a desired portion of flexible walls of the plunger shaft are exposed outside of the syringe bore;

positioning the syringe with the sealable luer in sealed condition lower than the plunger-bore plate;

hand-squeezing the flexible walls of the plunger shaft sufficiently to break the ampule within the plunger-shaft bore;

removing a pressure-equalizer cover from the plunger-bore plate;

allowing the sterile preparation to flow from the broken ampule into the syringe bore by means of a vacuum in the syringe bore and in the plunger bore in negative-pressure relationship to a fluid head of the sterile preparation;

reversing position of the syringe to where the sealable luer is above the plunger-bore plate;

unsealing the sealable luer, attaching a hypodermic needle to the sealable luer;

aspirating the syringe; and injecting sterile preparation from the syringe as desired.

* * * * *